United States Patent [19]

Eastlund et al.

[11] 4,208,587

[45] Jun. 17, 1980

[54] METHOD AND APPARATUS FOR ULTRAVIOLET CURING OF THREE DIMENSIONAL OBJECTS WITHOUT ROTATION

[75] Inventors: Bernard J. Eastlund, Olney; Charles H. Wood, Rockville; Robert W. Couch, Wheaton; Michael G. Ury, Bethesda, all of Md.

[73] Assignee: Fusion Systems Corp., Rockville, Md.

[21] Appl. No.: 719,209

[22] Filed: Aug. 31, 1976

[51] Int. Cl.² .......... A61K 27/02

[52] U.S. Cl. .......... 250/492 R; 250/372; 250/461 R

[58] Field of Search .......... 250/492, 372, 360, 461, 250/341, 492 R; 34/41, DIG. 10

[56] References Cited

U.S. PATENT DOCUMENTS

| | | | |
|---|---|---|---|
| 2,608,487 | 8/1952 | Kauffman et al. | 250/492 |
| 3,790,801 | 2/1974 | Coleman | 250/492 |
| 3,826,014 | 7/1974 | Helding | 34/41 |

*Primary Examiner*—Harold A. Dixon

*Attorney, Agent, or Firm*—Pollock, Vande Sande & Priddy

[57] ABSTRACT

A method and apparatus for curing three dimensional objects such as cylindrical two piece cans with ultraviolet light without having to rotate the cans, at conventional can line speeds and using a minimum number of lamp units. In a first embodiment, the cans are moved, without rotation, between at least a pair of ultraviolet lamp units so that the closest surfaces to the lamp units are substantially within the focal planes thereof. The lamp units are parallel to the direction of can movement or are rotated from that direction by a small angle with the lamp units of each pair being rotated by the same angle but in opposite senses. In a further embodiment, each lamp unit, instead of being faced by another lamp unit, is faced by a reflector to increase the cure speed attainable with the same number of lamp units.

34 Claims, 12 Drawing Figures

METHOD AND APPARATUS FOR ULTRAVIOLET CURING OF THREE DIMENSIONAL OBJECTS WITHOUT ROTATION

The present invention is directed to a method and apparatus for curing three dimensional objects with ultraviolet radiation and specifically is directed to a method and apparatus for uniformly curing the objects without rotating them.

In recent years, the graphic arts and packaging industries have turned to a process referred to as ultraviolet curing to solve the twin problems of strict emission control standards and the energy shortage in the drying of inks and coatings. Curing is produced by a polymerization reaction initiated by ultraviolet light—changing a component of the ink or coating from a liquid to solid state almost instantaneously. Since these inks and coatings do not contain solvents, they give essentially pollution-free printing.

As will be elucidated below, to provide for maximum intensity radiation, lamps for ultraviolet curing are typically highly focussed units with the substrate to be cured being placed in the focal plane. While this arrangement works well in the curing of flat or planar surfaces, curing of cylindrical objects such as collapsible metal tubes and rigid plastic containers and two-piece (i.e., seamless drawn and wall-ironed) beverage and beer cans requires more complicated mechanical systems in which the objects are rotated to attain a cure over the entire cylindrical surface.

The requirement of rotating cylindrical objects such as cans has presented several problems which the present invention obviates. The rotation can be accomplished through the use of mandrel pins, brush pins, eggbeater pins, or suction cups. In any event, equipment for rotating the cans is expensive and does not always provide trouble-free operation. The cans sometimes become unstable and fall off the pins or brushes which are used to rotate them. All of these problems of reliability, can stability, and wear become more serious at the higher production line speeds which are continuously sought by industrial users. Further, conventional two-piece can lines do not provide the necessary equipment for rotating the cans, so when it is desired to convert a conventional two-piece can line to a UV curing mode, it is necessary to substantially modify the can-handling portion of the line after the decorator to provide for the required rotation. This involves additional expense and complication which the solution of the present invention avoids.

It is therefore an object of the present invention to provide a method and apparatus for curing three dimensional objects with ultraviolet radiation without rotating the objects.

It is a further object of the invention to provide a method and apparatus for curing two-piece cans and other cylindrical objects with ultraviolet radiation without rotating the cans.

It is still a further object of the invention to provide a method and apparatus which provides a uniform cure in both the axial and azimuthal directions of the cans at conventional two-piece line speeds, and which uses relatively few lamp units.

The invention will be better understood by referring to the accompanying drawings, in which.

Figure 1:
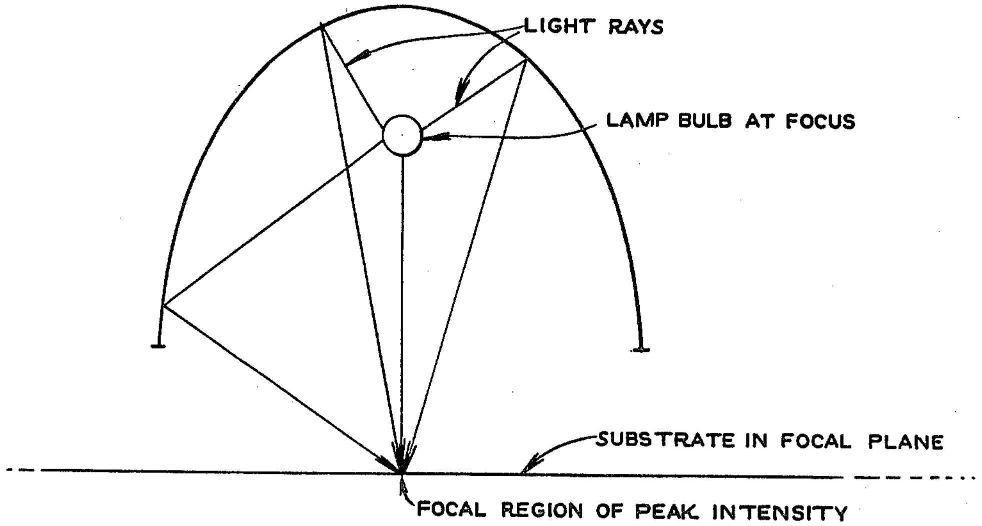
FIG. 1 illustrates a semi-elliptical reflector with a lamp bulb at the upper focus and the substrate to be cured at the lower focus.

Referring to FIG. 1, a typical light source used for ultraviolet curing consists of a reflector and a bulb. The reflector is used to focus the light from the bulb to a high intensity on the ink or coating to be polymerized. This is done because the cure rates of many inks and coatings depend on the peak intensity of ultraviolet light and most such materials exhibit an intensity threshold below which effective curing does not take place. Typically, the reflector is a half-ellipse in cross-section with the bulb lying along the locus of the foci of the cross-section. The substrate on which the UV-curable inks or coatings have been applied passes through the other foci of the ellipses. This arrangement, which is shown in cross-section in FIG. 1, insures that the rays of light from the bulb which are reflected from the half-ellipse, are directed toward a region close to the other foci. This produces a relatively narrow (typically ½" wide) strip of high intensity light the length of the bulb on the substrate.

Figure 2:
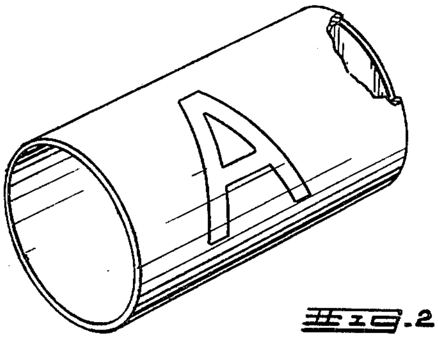
FIG. 2 shows a two-piece can having the letter A printed thereon.

While the above-described technique works quite well in the curing of UV-polymerizable inks and coatings on flat or planar surfaces, curing of such inks and coatings on multi-sided objects requires a more complicated arrangement. One such application which is of considerable commercial importance involves the curing of inks and coatings on the cylindrical exterior of two-piece cans. Such cans, which are widely used for beverages and beer, are formed initially out of a single piece of metal which is stamped into the shape of a cup and drawn out into a cylinder with a closed bottom. The second piece of the two-piece can is the top which is added after the can is filled. The can is coated and printed on its cylindrical exterior side-wall by special presses. Such a can is illustrated in FIG. 2, the printing being represented simply by the letter A on the outside of the can.

Figure 3:
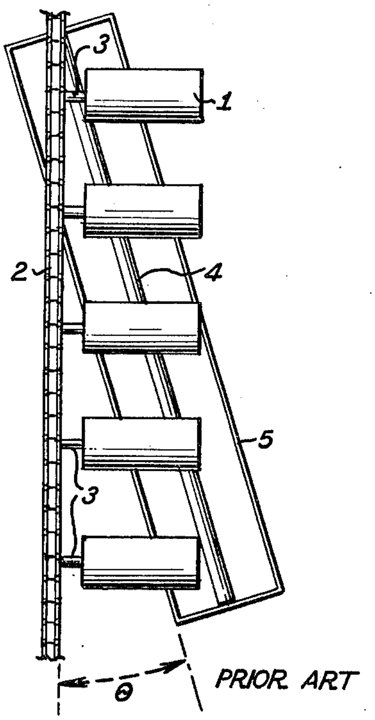
FIG. 3 is a plan view of the prior art UV curing apparatus in which the cans are rotated.

After decoration, if ultraviolet-curable inks or coatings are used, the can must be exposed to high intensity ultraviolet light over its entire exterior side-wall. The technique which is presently used for curing inks and coatings on cylindrical two-piece cans is illustrated in FIG. 3. The cans 1 are carried on a belt or pins or brushes 3, which are attached to moving chain 2, past a long lamp 4, 5, or an array of shorter lamps which are aligned so that the strip of ultraviolet light produced by the lamps is nearly perpendicular to the can axis. The lamps are inclined at a slight angle ($\theta$) to the perpendicular so that the strip of light covers the top of the side-wall at one end of the lamp array and the bottom of the side-wall at the other end. As the cans translate under the lamps, the mandrel pins or brushes are caused to rotate by mechanical means which causes the cans to rotate.

Figure 4:
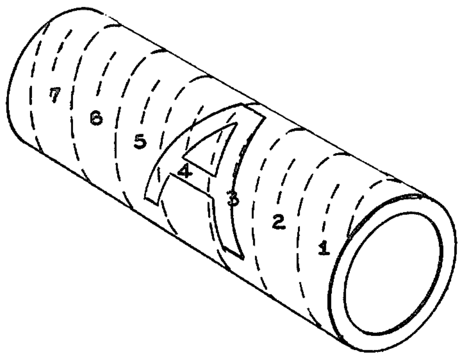
FIG. 4 shows the helical cure pattern obtained with the prior art arrangement of FIG. 3.

The principle is to rotate the can at a sufficiently rapid rate to expose all portions of the printed area to the high intensity UV light concentrated near the second focus of the elliptical reflector. This results in the helical cure pattern shown in FIG. 4 in which each strip (1), (2), (3), etc. is cured in turn as the can rolls under the lamp.

While the above-described technique has been used commercially, it has definite drawbacks which the present invention has been designed to overcome. Specifically, the requirement of having to rotate the cans has presented the problems enumerated above. The present invention accomplishes the same result as the prior art system without the mechanical and economical problems engendered by the rotation requirement.

Figure 5:
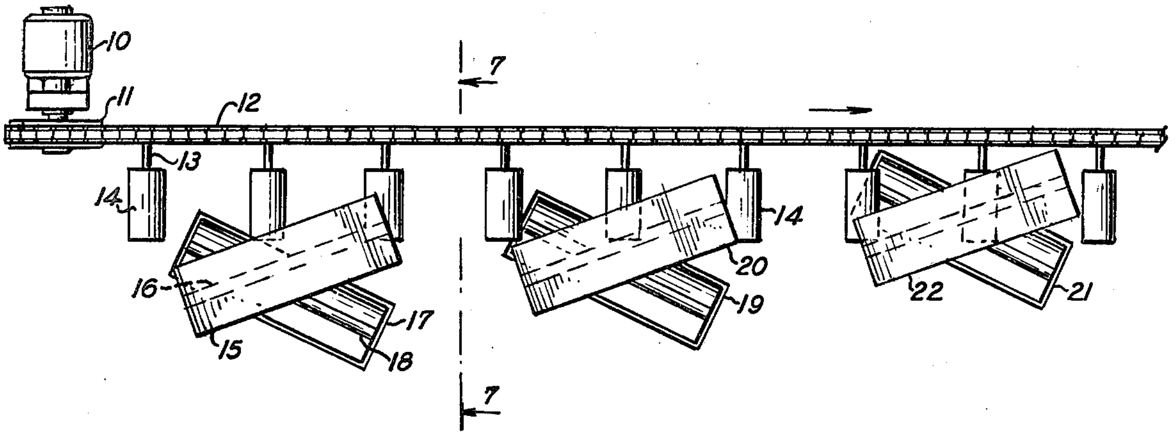
FIG. 5 is a top plan view of an embodiment of the invention.
Figure 6:
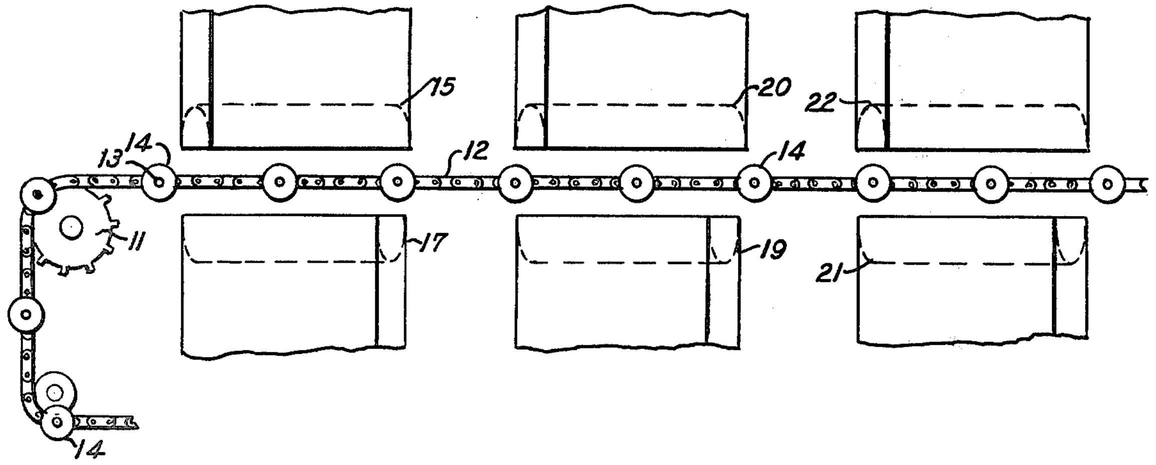
FIG. 6 is a side view of the embodiment of FIG. 5.
Figure 7:
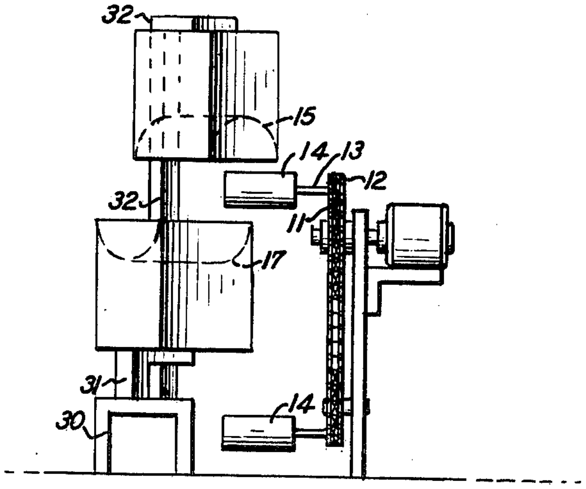
FIG. 7 is an end view of the embodiment of FIG. 5, additionally showing an illustrative mounting means for the lamp units.

An embodiment of the present invention is illustrated in FIGS. 5 to 7. Cans 14 are moved along the translation path by pins 13 which are mounted on chain 12 which is driven by motor 10. Unlike in the prior art system shown in FIG. 3, the transport belt or pin chain 12, 13 is the type found in conventional can lines and pins 13 do not rotate. Focused ultraviolet lamp unit 15, 16, comprised of lamp tube 16 and a housing including reflector 15, is disposed on one side of the translation path facing the path and focused ultraviolet lamp unit 18, 17 is disposed on the other side of the translation path facing the path so that cans traveling between the lamp units are irradiated by light rays from both lamp units.

Figure 9:
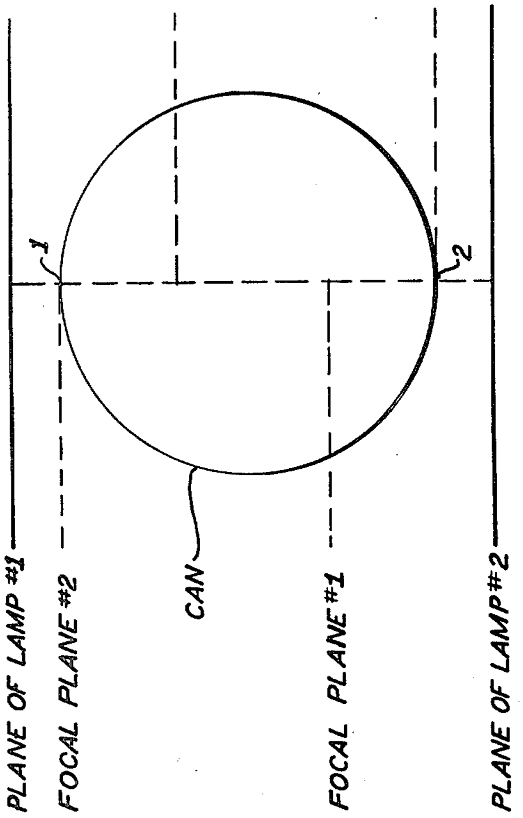
FIG. 9 is a diagrammatic illustration of the geometric aspects of the curing technique of the invention.
Figure 8:
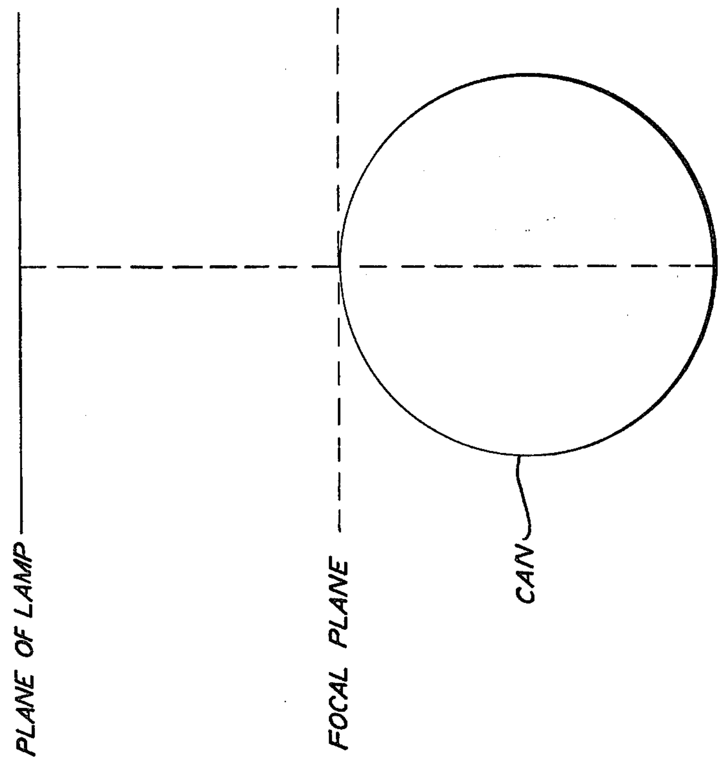
FIG. 8 is a diagrammatic illustration of the geometric aspects of the prior art curing technique.

As shown in FIG. 6, the lamp units of each pair are mounted so that their focal planes are parallel to each other. However, unlike the prior art system of FIG. 3, in which the closest surface of the can is located at the focal plane, in the embodiment of the present invention, the cans are located substantially closer to the lamp units than the focal planes. This is clearly illustrated by comparing FIG. 8 which represents the prior art in which the closest region of the can is at or near the focal plane with FIG. 9 which represents the invention in which the can is substantially closer than the focal plane or focal planes. Thus, it is seen that in FIG. 9 nearest point 1 to lamp unit 1 is substantially closer to the lamp unit than focal plane 1 and nearest point 2 to lamp unit 2 is substantially closer to the lamp unit than focal plane 2. In an experimental embodiment of the invention, the cans were 2½" in diameter, points 1 and 2 were locatd 3/8" from the corresponding lamp units and the focal planes were located 2¼" from the lamp units.

Figure 10:
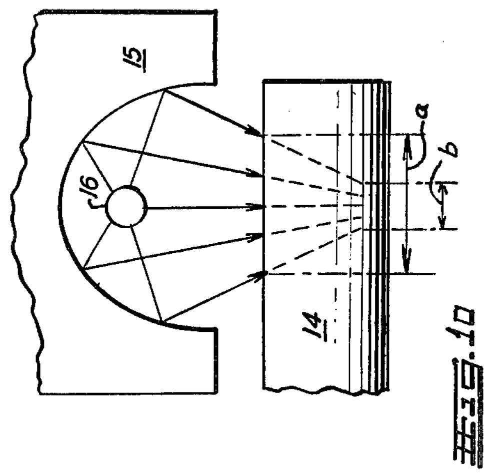
FIG. 10 is a ray diagram of the embodiment of FIG. 5 looking end-wise at a lamp unit.

The unique arrangement of the invention, by locating the cans substantially closer to the lamp units than the focal planes, utilizes the unfocused light rays emitted by the lamps, which provide a cure over a greater area of a three dimensional object than do the focused rays. Thus, in FIG. 10 it is seen that area a covered by the unfocused rays intercepted by the surface of the can is larger than area b which would be intercepted by the focused rays. The fact that there are fewer light rays per unit area at area a is to some extent counteracted by that fact that the surface of the can is closer to the source, resulting in high enough intensity for effective curing.

Figure 11:
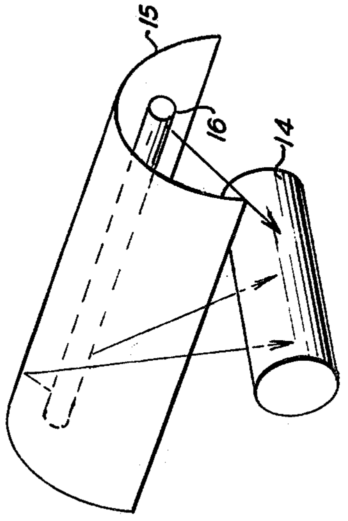
FIG. 11 is a ray diagram of the embodiment of FIG. 5 looking side-wise at a lamp unit.

Also, the present invention utilizes the iostropic rays coming from the length of the lamp and reflector to effectively cure the three dimensional object. Thus, referring to FIG. 11, it is seen that every point along the lamp bulb emits light isotropically and there are many rays, both direct from the bulb, and reflected, which are incident on the can at different angles. These rays are used to cure the "sides" of the can, and are the reason why only two lamp units can cure an area which extends 360° around the can.

As noted above, to be commercially acceptable, the cure provided must be uniform around the surface of the can, and must be attainable at conventional line speeds not using an unduly large number of light sources. This means that the axial extent of the surface which is cured over a full 360° of azimuthal extent by any pair of lamp units should be as large as possible and must be as uniformly cured as possible. It has been found that this occurs when the lamp units are oriented so that the long dimensions thereof make a small angle with the direction of translation, each lamp unit being angularly offset from the direction of translation in the opposite sense as the other lamp unit of the pair. Thus, in FIG. 5, lamp units 18, 17 and 16, 15 are angularly offset from the direction of translation in opposite senses and, in one embodiment, each of the lamp units was offset by 6° from the direction of translation. While this angle can vary for optimization in individual applications, for best results, the angle should not exceed 12°. As shown in FIG. 5, the lamp units of each pair cross each other at approximately the mid-area thereof so that the pair is symmetrical about a mid-line. The lamp units can be mounted so as to remain properly positioned by any mechanical expedient, and a variety of such mounting means will occur to those skilled in the art and form no part of the present invention. However, by way of example, platform 30 is shown in FIG. 7 and is seen to have supports 31 and 32 projecting vertically therefrom for mounting lamp units 18, 17 and 16, 15, respectively.

If a pair of lamp units are mounted parallel to one another, and parallel to the direction of can movement (i.e., with no angular offset), a surface cure of 360° azimuthal extent and moderate axial extent is achieved. This is satisfactory for a number of applications in which the additional axial extent of cure achieved with a small angular offset is not of significant benefit.

Since the relative dimensions of commercially available light sources useful for carrying out the present invention and commercial cans are such that one pair of lamp units will cure an azimuthal strip only along a part of the axial extent of the can, more than one pair of lamp units may be necessary to cure the entire surface of the can. As shown in FIG. 5, a second, and further pair of lamp units are provided if necessary, with each pair being offset in the axial direction from the adjacent pair to provide several overlapping azimuthal cure strips along the axial extent of the cans. With a Fusion System 10" long ultraviolet lamp unit pair at 6° angular offsets from the direction of can movement, a 3" axially extending strip was cured with the can moving at over 300 feet per minute, a typical line speed. Thus, a system to cure a typical 6" high can requires only two pairs or a total of four lamp units while a six lamp array such as is shown in FIGS. 5 and 6 would be able to cure a 350 feet per minute can line with overlap in the cured strips. This line speed, when using a pin-chain with 5¼" spacings between pins, is the equivalent of 800 cans per minute which is an industry standard.

Figure 12:
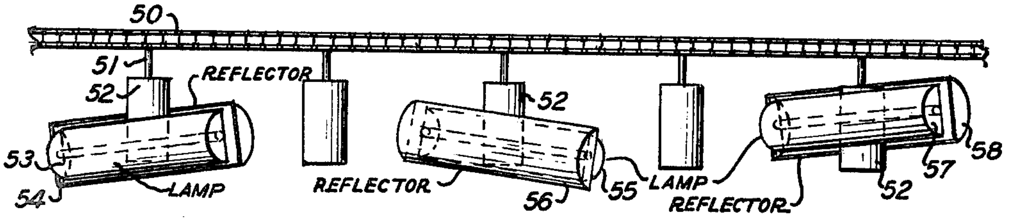
FIG. 12 is an illustration of a further embodiment of the invention.

A further embodiment of this invention is shown in FIG. 12. Referring to the Figure, it is seen that pin chain 50, 51 transports the cans 52 past the lamp units. As in the first embodiment, the lamp units are parallel to the direction of can movement or at a slight angular offset with respect thereto. However, instead of pairs of lamps facing one another, each lamp unit in the embodiment of FIG. 12 is faced by a reflector. Thus, it is seen that lamps 53, 55 and 57 are faced by the respective reflectors 54, 56 and 58. The reflectors, which are generally parabolic in cross-section and are wider but shallower than the elliptical cross-section reflectors employed in the lamp units themselves, are placed very close to the unilluminated side of the can, directly facing the lamp unit. The function of the reflectors is to capture the light rays which do not intersect the can and to reflect them back onto the unilluminated side. At typical line speeds, this provides some, but not complete, curing of a full azimuthal strip of can surface. Thus, it is still necessary to use pairs of lamp units at the same axial position on the can height but illuminating opposite sides of the can.However, in this embodiment, the two lamps in each pair, such as lamp units 53 and 55 in FIG. 12, are separated from one another along the direction of can movement and each faces a reflector. The effect of the reflectors is to increase the line speed at which complete curing takes place with a given number of lamp units. With a pair of 10" Fusion Systems ultraviolet lamp units at 6° angular offsets and reflectors in this embodiment, a 3" axially extending strip was cured with the can moving at 400 feet per minute; when the pair of lamps were used at a common location along the can path without reflectors, the same curing was accomplished only at a speed of 325 feet per minute.

It should be noted that while the invention has been illustrated in conjunction with pin chains for providing the required can translation, other modes of can movement such as brush-pin, conveyor belt, magnetic and vacuum conveyors, and others, may be used, the essential requirement of the present invention being only the spatial relationship between the lamp units and the cans as the cans are moved. Further, the invention is not limited to the curing of cans, but encompasses the uniform curing of three dimensional objects broadly.

Further, while we have described and illustrated an embodiment of our invention, we wish it to be understood that we intend to cover all modifications thereof which would be apparent to one skilled in the art and which come within the spirit and scope of our invention.

What is claimed is:

1. A method of curing three dimensional cylindrical objects with a plurality of ultraviolet lamp units without rotating the objects, comprising the steps of;

providing at least a pair of focussed ultraviolet lamp units, each of which focusses the light emitted therefrom at a focal plane, defining a translation path for said three dimensional objects, said focal planes of said lamp units being parallel to each other and parallel to said translation path, locating one of said lamp units on one side of said translation path generally facing said path, and the other of said lamp units on the other side of said path generally facing said path, and moving said objects along said translation path close enough to said lamp units so that parts of each object are substantially closer to said lamp units than said focal planes, said lamp units being linear lamp units having a long dimension and a short dimension, and being situated opposite each other across said translation path with the long dimension of each lamp unit being at an angle of at least 78° with the cylindrical axis of said moving said cylindrical objects.

2. The method of claim 1 wherein the said long dimension is at an acute angle with respect to said translation path.

3. The method of claim 2 wherein said cylindrical objects are moved with their cylindrical axes perpendicular to said translation path.

4. The method of claim 3 wherein the lamp units of said pair of lamp units are situated so that the respective long dimensions of said lamp units are at the same acute angle with respect to said translation path, but are rotated in opposite senses from the direction of said path.

5. The method of claim 4 wherein said lamps are situated so that said respective long dimensions cross each other at an acute angle.

6. The method of claim 5 wherein said respective long dimensions cross each other at an angle of less than 24°.

7. The method of claim 6 wherein said lamp units of said pair of lamp units are of the same length and wherein said respective long dimensions cross each other at approximately the mid-areas thereof.

8. The method of claim 11 wherein a plurality of said pairs of ultraviolet lamp units are provided along said translation path, with adjacent pairs being offset from each other in the direction perpendicular to said translation path.

9. A method of curing three dimensional objects with a plurality of ultraviolet lamp units without rotating the objects, comprising the steps of;

providing at least a pair of focussed ultraviolet lamps units, each of which focusses the light emitted therefrom at a focal plane, defining a translation path for said three dimensional objects, locating one of said lamp units on one side of said translation path generally facing said path, and the other of said lamp units on the other side of said path generally facing said path, and moving said objects along said translation path close enough to said lamp units so that parts of each object are substantially closer to said lamp units than said focal planes, said lamp units being linear lamp units having a long dimension and a short dimension, and being situated opposite each other across said translation path with the long dimension of the respective lamp units making an acute angle with the translation path.

10. A method of curing three dimensional objects with a plurality of ultraviolet lamp units without rotating the objects, comprising the steps of:

providing at least a pair of focussed ultraviolet lamp units, each of which focusses the light emitted therefrom at a focal plane, defining a translation path for said three dimensional objects, locating one of said lamp units on one side of said translation path generally facing said path, and the other of said lamp units on the other side of said path generally facing said path, and moving said objects along said translation path close enough to said lamp units so that parts of each object are substantially closer to said lamp units than said focal planes, said lamp units of said pair being separated from each other in the translation path direction, and each lamp unit having a reflector opposite thereto across said translation path, said reflectors being parabolic reflectors.

11. A method of curing at least a three-dimensional section of a single three-dimensional object with a single pair of elongated ultraviolet light source means without rotating the object, comprising the steps of;

providing a single pair of elongated ultraviolet light source means, one of said light source means comprising the combination of an ultraviolet lamp and a reflector, and the other of said source means comprising a reflecting means for reflecting light which is emitted by said combination source means, defining a translation path for said single object, disposing said object in said translation path, the length of each elongated light source means being substantially greater than the length of said single three-dimensional object in the translation path direction, locating one of said light source means on one side of said translation path generally facing said path, and the other of said light source means on the other side of the path, generally facing said path, and moving said single object along said translation path close enough to said elongated light source means so that a forward facing surface portion of said section of said object, which portion lies in a plane perpendicular to said translation path and is a portion to be cured, is irradiated across its entirety by light rays which are isotropically emitted from points along the length of the elongated light source means in front of the object, so that as the object progresses along the translation path, the surface portions of the object generally facing said light source means are cured by light rays emitted from the portions of the source means that the object is between, and the forward facing surface portion is cured by said isotropically emitted rays emitted from points on the source means which are in front of the object.

12. A method of curing at least a three-dimensional section of a single three-dimensional object with a single pair of elongated ultraviolet light source means without rotating the object, comprising the steps of;

providing a single pair of elongated ultraviolet light source means, each of said light source means comprising a focussed light source means which focusses the light emitted therefrom at a focal plane, defining a translation path for said single object, disposing said object in said translation path, the length of each elongated light source means being substantially greater than the length of said single three-dimensional object in the translation path direction, locating one of said light source means on one side of said translation path generally facing said path, and the other of said light source means on the other side of the path, generally facing said path, and moving said single object along said translation path close enough to said light source means so that parts of said object are substantially closer to said light source means than said focal planes and close enough to said light source means so that a forward facing surface portion of said section of said object, which portion lies in a plane perpendicular to said translation path and is a portion to be cured, is irradiated across its entirety by light rays which are isotropically emitted from points along the length of the elongated light source means in front of the object, so that as the object progresses along the translation path, the surface portions of the object generally facing said light source means are cured by light rays emitted from the portions of the source means that the object is between, and the forward facing surface portion is cured by said isotropicaly emitted rays emitted from points on the source means which are in front of the object.

13. A method of curing at least a three-dimensional section of a single three-dimensional object having a longitudinal axis with a single pair of elongated ultraviolet light source means without rotating the object, comprising the steps of;

providing a single pair of elongated ultraviolet light source means, defining a translation path for said single object, disposing said object in said translation path, the length of each elongated light source means being substantially greater than the length of said single three-dimensional object in the translation path direction, locating one of said light source means on one side of said translation path generally facing said path, and the other of said light source means on the other side of the path, generally facing said path, said elongated light source being oriented so that their respective long dimensions make an angle with said longitudinal axis of said object of other than 0° or 90°, and moving said single object along said translation path close enough to said elongated light source means so that a forward facing surface portion of said section of said object, which portion lies in a plane perpendicular to said translation path and is a portion to be cured, is irradiated across its entirety by light rays which are isotropically emitted from points along the length of the elongated light source means in front of the object, so that as the object progresses along the translation path, the surface portions of the object generally facing said light source means are cured by light rays emitted from the portions of the source means that the object is between, and the forward facing surface portion is cured by said isotropically emitted rays emitted from points on the source means which are in front of the object.

14. The method of claim 13 wherein the light source means are oriented so that the long dimensions of the respective source means are parallel to each other.

15. The method of claim 14 wherein one of said light source means comprises an ultraviolet lamp unit and the other of said source means comprises a reflecting means.

16. The method of claim 15 wherein a plurality of pairs of light source means are provided, said pairs being disposed so that the long dimensions of every other pair are parallel but displaced from each other in the direction perpendicular to the direction of said translation path and so that the long dimensions of every adjacent pair are at an acute angle to each other.

17. The method of claim 13 wherein the light source means are oriented so that the long dimensions of the respective sources cross each other at an angle other than 90°.

18. The method of claim 17 wherein said light source means are of substantially equal length and wherein the long dimensions of the respective source means cross each other at an acute angle at substantially the mid-portions thereof.

19. The method of claim 17 wherein said object is an elongated object which is disposed with its longitudinal axis perpendicular to the direction of said translation path.

20. The method of claim 18 wherein a plurality of pairs of light source means are provided, each of said pairs being offset from the adjacent pair in the direction perpendicular to the direction of said translation path.

21. The method of claim 17 wherein each of said light source means comprises an ultraviolet lamp unit.

22. The method of claim 17 wherein the long dimensions of the respective sources make an angle of at least 78° with said longitudinal axis.

23. The method of claim 22 wherein said object is a cylindrical can.

24. An apparatus for curing at least a three-dimensional section of a single three-dimensional object with a single pair of elongated ultraviolet light source means without rotating the object, comprising, a single pair of elongated ultraviolet light source means, each comprising a focussed light source means which focusses the light emitted therefrom at a focal plane, each light source means being located on one side of a translation path for said single object, the length of each of said light source means being substantially greater than the length of said object in said translation path direction when said object is disposed in said path, and means for moving said object along said translation path close enough to said light source means so that parts of said object are substantially closer to said light source means than said focal planes and close enough to said light source means so that a forward facing surface portion of said section of said object, which portion lies in a plane perpendicular to said translation path and is a portion to be cured, is irradiated across its entirety by light rays which are isotropically emitted from points along the length of the elongated light source means in front of the object, so that as the object progresses along the translation path, the surface portion of the object generally facing said light source means is cured by the light rays emitted from the portions of the source means that the object is between, and the forward facing surface portion is cured by said isotropically emitted rays which are emitted from points of the source means which are ahead of the object.

25. The apparatus of claim 24 wherein each of said light source means comprises an ultraviolet lamp unit, comprised of an ultraviolet lamp and a reflector.

26. The apparatus of claim 24 wherein one of said light source means comprises an ultraviolet lamp unit and the other of said source means comprises a reflecting means for reflecting light which is emitted by said ultraviolet lamp unit.

27. The apparatus of claim 26 wherein a plurality of said pairs of light source means are provided, said pairs being disposed so that the long dimensions of every other pair are parallel to each other but displaced from each other in the direction perpendicular to the translation path direction and so that the long dimensions of every adjacent pair are at an acute angle to each other.

28. An apparatus for curing at least a three dimensional section of a single three dimensional object having a longitudinal axis with a single pair of elongated ultraviolet light source means without rotating the object, comprising, a single pair of elongated ultraviolet light source means, each light source means being located on one side of a translation path for said single object, said light source means being oriented so that their respective long dimensions make an angle with said longitudinal axis of said object of other than 0° or 90° when said object is disposed in said path, the length of each of said light source means being substantially greater than the length of said object in said translation path direction when said object is disposed in said path, and means for moving said object along said translation path close enough to said elongated light source means so that a forward facing surface portion of said section of said object, which portion lies in a plane perpendicular to said translation path and is a portion to be cured, is irradiated across its entirety by light rays which are isotropically emitted from points along the length of the elongated light source means in front of the object, so that as the object progresss along the translation path, the surface portion of the object generally facing said light source means is cured by the light rays emitted from the portions of the source means that the object is between, and the forward facing surface portion is cured by said isotropically emitted rays which are emitted from points of the source means which are ahead of the object.

29. The apparatus of claim 28 wherein said light source means are oriented so that the long dimensions of the respective sources cross each other at an angle other than 90°.

30. The apparatus of claim 29 wherein said light source means are of substantially equal length and wherein the long dimensions of the respective source means cross each other at an acute angle at substantially the mid-portions thereof.

31. The apparatus of claim 30 wherein said object is an elongated object, and said means for moving comprises means for moving said object with its longitudinal axis perpendicular to the direction of said translation path.

32. The apparatus of claim 31 wherein the long dimensions of the respective sources make an angle of at least 78° with said lonigitudinal axis.

33. The apparatus of claim 32 wherein said object is a cylindrical can.

34. The apparatus of claim 33 wherein a plurality of pairs of said light source means are provided, each of said pairs being offset from the adjacent pair in the direction perpendicular to the direction of said translation path.

* * * * *